(12) United States Patent
Utku (10) Patent No.: US 9,096,654 B2
(45) Date of Patent: Aug. 4, 2015

(54) PEPTIDES CAPABLE OF MODULATING THE FUNCTION OF TIRC7

(75) Inventor: Nalân Utku, Dortmund (DE)

(73) Assignee: CELLACT PHARMA GMBH, Dortmund (DE)

( * ) Notice: Subject to any disclaimer, the term of this patent is extended or adjusted under 35 U.S.C. 154(b) by 92 days.

(21) Appl. No.: 13/338,771

(22) Filed: Dec. 28, 2011

(65) Prior Publication Data

US 2014/0154279 A1 Jun. 5, 2014

Related U.S. Application Data

(63) Continuation of application No. 11/914,628, filed as application No. PCT/EP2006/004690 on May 17, 2006, now abandoned.

(30) Foreign Application Priority Data

May 17, 2005 (EP) .................................. 05010684

(51) Int. Cl.
*C07K 14/00* (2006.01)
*C07K 9/00* (2006.01)
*C07K 14/705* (2006.01)
*A61K 38/17* (2006.01)

(52) U.S. Cl.
CPC ............... *C07K 14/001* (2013.01); *A61K 38/17* (2013.01); *C07K 14/705* (2013.01); *C07K 9/00* (2013.01)

(58) Field of Classification Search
CPC ............................ C07K 14/001; C07K 14/705
See application file for complete search history.

(56) References Cited

FOREIGN PATENT DOCUMENTS

| WO | WO 99/11782 | * | 3/1999 | ............ C12N 15/12 |
|---|---|---|---|---|
| WO | WO 99/11782 A | | 3/1999 | |
| WO | WO 02/090544 | * | 11/2002 | ............ C12N 15/12 |
| WO | WO 03/025000 | * | 3/2003 | ............ C07K 14/00 |
| WO | WO 03/025000 A | | 3/2003 | |
| WO | WO 03/025000 A2 | | 3/2003 | |

OTHER PUBLICATIONS

N. Utku et al.: Prevention of acute allograft rejection by antibody targeting of TIRC7, a novel T cell membrane protein, in: Cell Press, vol. 9, Oct. 1998.
Utku, Nâlan, et al., "Prevention of Acute Allograft Rejection by Antibody Targeting of TIRC7, a Novel T Cell Membrane Protein," *Immunity*, Oct. 1998, vol. 9, p. 509-518.

\* cited by examiner

*Primary Examiner* — Amber D Steele
(74) *Attorney, Agent, or Firm* — Saliwanchik, Lloyd & Eisenschenk (57) ABSTRACT

Provided are peptides capable of inhibiting proliferation of peripheral blood mononuclear cells (PBMCs) derived from the third extracellular domain of T-cell immune response cDNA7 (TIRC7) costimulatory molecule are described. Compositions comprising such peptides and their use for the treatment of immune diseases are provided.

10 Claims, 1 Drawing Sheet

A. 3rd extracellular domain of TIRC7 hrhrrrlrrr padrqeenka glldlpdasv ngwssdeeka ggldddeeeae lvpsevlmhq aihtiefclg cv (SEQ ID NO: 1)

Peptide 7 d    hrhrrrlrrrp (SEQ ID NO: 2)

B. D46M    drqeenka glldlpdasv ngwssdeeka ggldddeeeae lvpsevlm (SEQ ID NO: 3)

A61V    adrqeenka glldlpdasv ngwssdeeka ggldddeeeae lvpsevlmhq aihtiefclg cv (SEQ ID NO: 4)

C. TEX40-C    DHFR hrhrrrlrrr padrqeenka glldlpdasv ngwssdeeka ggldddeeeae lvpsevlmhq aihtief (SEQ ID NO: 5)

TEX40+C    DHFR hrhrrrlrrr padrqeenka glldlpdasv ngwssdeeka ggldddeeeae lvpsevlmhq aihtiefclg cv (SEQ ID NO:1)

TEX60-C    mv hrhrrrlrrr padrqeenka glldlpdasv ngwssdeeka ggldddeeeae lvpsevlmhq aihtief rshhhhhh (SEQ ID NO: 6)

TEX60+C    mv hrhrrrlrrr padrqeenka glldlpdasv ngwssdeeka ggldddeeeae lvpsevlmhq aihtiefclg cv srshhhhhh (SEQ ID NO: 7)

ions, i.e. Th1 and Th2, which are distinguishable by their pattern of cytokine production and characterize the mode of cellular immune response. The T-cell response is initiated by the interaction of the antigen-specific T-cell receptor (TCR) with peptide presented by major histocompatibility complex (MHC) molecules on the surface of antigen presenting cells (APCs). Additional signals are provided by a network of receptor-ligand interactions mediated by a number of membrane proteins such as CD28/CTLA4 and B7, CD40/CD40L, LFA-I and ICAM-I (Lenschow, Science 257 (1992), 789-792; Linsley, Annu. Rev. Immunol. 11 (1993), 191-212; Xu, Immunity 1 (1994), 423-431; Bachmann, Immunity 7 (1997), 549-557; Schwartz. Cell 71 (1992), 1065-1068), collectively called costimulatory signals (Perez, Immunity 6 (1997), 411-417). These membrane proteins can alter T-cell activation in distinct ways (Bachmann, Immunity 7 (1997), 549-557) and regulate the immune response by the integration of positive and negative signals provided by these molecules (Bluestone, Immunity 2 (1995), 555-559; Perez, Immunity 6 (1997), 411-417). Many of the agents which are effective in modulating the cellular immune response either interfere with the T-cell receptor (Cosimi, Transplantation 32 (1981), 535-539) block costimulatory signaling (Larsen, Nature 381 (1996), 434-438; Blazar J. Immuno. 157 (1996), 3250-3259; Kirk, Proc. Natl. Acad. Sci. USA 94 (1997), 8789-8794; Linsley, Science 257 (1992), 792-95; Turka, Proc. Natl. Acad. Sci. USA 89 (1992), 11102-11105) or inhibit intracellular activation signals downstream from these primary cell membrane triggers (Schreiber and Crabtree, Immunology Today 13 (1992), 136-42). Therapeutic prevention of T-cell activation in organ transplantation and autoimmune diseases presently relies on panimmunosupressive drugs interfering with downstream intracellular events. Specific modulation of the immune response remains a longstanding goal in immunological research.

SEQUENCE LISTING

<160> NUMBER OF SEQ ID NOS: 8

<210> SEQ ID NO 1
<211> LENGTH: 72
<212> TYPE: PRT
<213> ORGANISM: Artificial
<220> FEATURE:
<223> OTHER INFORMATION: TIRC7 peptide
<220> FEATURE:
<221> NAME/KEY: PEPTIDE

```
<222> LOCATION: (1)..(72)
<223> OTHER INFORMATION: Third extracellular domain of TIRC7

<400> SEQUENCE: 1

His Arg His Arg Arg Leu Arg Arg Arg Pro Ala Asp Arg Gln Glu
1               5                   10                  15

Glu Asn Lys Ala Gly Leu Leu Asp Leu Pro Asp Ala Ser Val Asn Gly
            20                  25                  30

Trp Ser Ser Asp Glu Glu Lys Ala Gly Gly Leu Asp Asp Glu Glu Glu
        35                  40                  45

Ala Glu Leu Val Pro Ser Glu Val Leu Met His Gln Ala Ile His Thr
    50                  55                  60

Ile Glu Phe Cys Leu Gly Cys Val
65                  70

<210> SEQ ID NO 2
<211> LENGTH: 11
<212> TYPE: PRT
<213> ORGANISM: Artificial
<220> FEATURE:
<223> OTHER INFORMATION: TIRC7 peptide
<220> FEATURE:
<221> NAME/KEY: PEPTIDE
<222> LOCATION: (1)..(11)
<223> OTHER INFORMATION: Peptide 7d

<400> SEQUENCE: 2

His Arg His Arg Arg Leu Arg Arg Arg Pro
1               5                   10

<210> SEQ ID NO 3
<211> LENGTH: 46
<212> TYPE: PRT
<213> ORGANISM: Artificial
<220> FEATURE:
<223> OTHER INFORMATION: TIRC7 peptide
<220> FEATURE:
<221> NAME/KEY: PEPTIDE
<222> LOCATION: (1)..(46)
<223> OTHER INFORMATION: Peptide D46M

<400> SEQUENCE: 3

Asp Arg Gln Glu Glu Asn Lys Ala Gly Leu Leu Asp Leu Pro Asp Ala
1               5                   10                  15

Ser Val Asn Gly Trp Ser Ser Asp Glu Glu Lys Ala Gly Gly Leu Asp
            20                  25                  30

Asp Glu Glu Glu Ala Glu Leu Val Pro Ser Glu Val Leu Met
        35                  40                  45

<210> SEQ ID NO 4
<211> LENGTH: 61
<212> TYPE: PRT
<213> ORGANISM: Artificial
<220> FEATURE:
<223> OTHER INFORMATION: TIRC7 peptide
<220> FEATURE:
<221> NAME/KEY: PEPTIDE
<222> LOCATION: (1)..(61)
<223> OTHER INFORMATION: Peptide A16V

<400> SEQUENCE: 4

Ala Asp Arg Gln Glu Glu Asn Lys Ala Gly Leu Leu Asp Leu Pro Asp
1               5                   10                  15

Ala Ser Val Asn Gly Trp Ser Ser Asp Glu Glu Lys Ala Gly Gly Leu
            20                  25                  30
```

```
Asp Asp Glu Glu Glu Ala Glu Leu Val Pro Ser Glu Val Leu Met His
        35                  40                  45

Gln Ala Ile His Thr Ile Glu Phe Cys Leu Gly Cys Val
    50                  55                  60

<210> SEQ ID NO 5
<211> LENGTH: 67
<212> TYPE: PRT
<213> ORGANISM: Artificial
<220> FEATURE:
<223> OTHER INFORMATION: TIRC7 peptide
<220> FEATURE:
<221> NAME/KEY: PEPTIDE
<222> LOCATION: (1)..(67)
<223> OTHER INFORMATION: Peptide TEX40-C expressed without the
      C-terminal part of TIRC7

<400> SEQUENCE: 5

His Arg His Arg Arg Arg Leu Arg Arg Arg Pro Ala Asp Arg Gln Glu
1               5                  10                  15

Glu Asn Lys Ala Gly Leu Leu Asp Leu Pro Asp Ala Ser Val Asn Gly
            20                  25                  30

Trp Ser Ser Asp Glu Glu Lys Ala Gly Gly Leu Asp Asp Glu Glu Glu
        35                  40                  45

Ala Glu Leu Val Pro Ser Glu Val Leu Met His Gln Ala Ile His Thr
    50                  55                  60

Ile Glu Phe
65

<210> SEQ ID NO 6
<211> LENGTH: 75
<212> TYPE: PRT
<213> ORGANISM: Artificial
<220> FEATURE:
<223> OTHER INFORMATION: TIRC7 peptide
<220> FEATURE:
<221> NAME/KEY: PEPTIDE
<222> LOCATION: (1)..(75)
<223> OTHER INFORMATION: Peptide TEX60-C expressed without the
      C-terminal part of TIRC7

<400> SEQUENCE: 6

His Arg His Arg Arg Arg Leu Arg Arg Arg Pro Ala Asp Arg Gln Glu
1               5                  10                  15

Glu Asn Lys Ala Gly Leu Leu Asp Leu Pro Asp Ala Ser Val Asn Gly
            20                  25                  30

Trp Ser Ser Asp Glu Glu Lys Ala Gly Gly Leu Asp Asp Glu Glu Glu
        35                  40                  45

Ala Glu Leu Val Pro Ser Glu Val Leu Met His Gln Ala Ile His Thr
    50                  55                  60

Ile Glu Phe Arg Ser His His His His His
65                  70                  75

<210> SEQ ID NO 7
<211> LENGTH: 81
<212> TYPE: PRT
<213> ORGANISM: Artificial
<220> FEATURE:
<223> OTHER INFORMATION: TIRC7 peptide
<220> FEATURE:
<221> NAME/KEY: PEPTIDE
<222> LOCATION: (1)..(81)
<223> OTHER INFORMATION: Peptide TEX60+C expressed with the C-terminal
      part of TIRC7
```

```
<400> SEQUENCE: 7

His Arg His Arg Arg Leu Arg Arg Arg Pro Ala Asp Arg Gln Glu
1               5                   10                  15

Glu Asn Lys Ala Gly Leu Leu Asp Leu Pro Asp Ala Ser Val Asn Gly
            20                  25                  30

Trp Ser Ser Asp Glu Glu Lys Ala Gly Gly Leu Asp Asp Glu Glu Glu
        35                  40                  45

Ala Glu Leu Val Pro Ser Glu Val Leu Met His Gln Ala Ile His Thr
    50                  55                  60

Ile Glu Phe Cys Leu Gly Cys Val Ser Arg Ser His His His His His
65                  70                  75                  80

His

<210> SEQ ID NO 8
<211> LENGTH: 10
<212> TYPE: PRT
<213> ORGANISM: Artificial
<220> FEATURE:
<223> OTHER INFORMATION: VLA-4 fibronectin peptide (portion)

<400> SEQUENCE: 8

Gly Pro Glu Ile Leu Asp Val Pro Ser Thr
1               5                   10
```

US 9,096,654 B2

PEPTIDES CAPABLE OF MODULATING THE FUNCTION OF TIRC7

CROSS REFERENCE TO A RELATED APPLICATION

This application is a Continuation Application of U.S. patent application Ser. No. 11/914,628, filed Jul. 9, 2013 (now abandoned); which is a National Stage Application of International Application Number PCT/EP2006/004690, filed May 17, 2006; which claims priority to European Patent Application No. 05010684.8, filed May 17, 2005; all of which are incorporated herein by reference in their entirety.

The Sequence Listing for this application is labeled "SeqList-replace.txt", which was created on Feb. 16, 2015, and is 6 KB. The entire content is incorporated herein by reference in its entirety.

FIELD OF THE INVENTION

The present invention relates to peptides capable of modulating the function (e.g., signaling or adhesive activities) of T-cell immune response cDNA 7 (TIRC7) and/or its ligand. In particular, the peptides of the invention are capable of suppressing the proliferation of activated cells of the immune system. Furthermore, the present invention relates to compositions comprising said peptides and to methods of modulating immune cell proliferation, and treating immune response related diseases.

BACKGROUND OF THE INVENTION

T-cell activation is a serial process involving multiple signaling pathways and sequential changes in gene expression resulting in differentiation of T-cells into distinct subpopulations, i.e. Th1 and Th2, which are distinguishable by their pattern of cytokine production and characterize the mode of cellular immune response.

In view of the need for therapeutic means for the treatment of diseases related to immune responses of the human body, the technical problem of the present invention is to provide means and methods for modulation of the immune response in a subject. The solution to said technical problem is achieved by providing the embodiments characterized in the claims, and described further below.

BRIEF SUMMARY OF THE INVENTION

The present invention relates to a peptide capable of inhibiting proliferation of peripheral blood mononuclear cells (PBMCs), comprising a fragment of the amino acid sequence from the third extracellular domain of T cell immune response cDNA 7 (TIRC7) protein.

DETAILED DISCLOSURE

Without intending to be bound by theory, it is believed that the peptides derived from TIRC7 and described herein are capable of modulating the function (e.g., signaling or adhesive activities) of TIRC7, its family members and/or their ligands, for example by interfering with the interaction of TIRC7 with its ligand. The term "interfering with the interaction of TIRC7 with its ligand" means in accordance with the present invention that said peptide or analog or derivative thereof is capable of inhibiting and/or modulating the interaction of TIRC7 with its corresponding ligand. Since the interaction of TIRC7 with its ligand(s) modulates events which are valuable in the course of immune responses such peptide should also be capable of modulating immune responses. In accordance with the present invention said peptide preferably interacts with the TIRC7-ligand, for example by specifically binding to said ligand. The term "ligand" includes small molecules and soluble binding proteins as well as membrane associated receptors. "Specifically binding" means "specifically interacting with" whereby said interaction may be, inter alia, covalently, non-covalently and/or hydrophobic. However, irrespective the theory behind the molecular mechanism of action, the peptides of the invention can be characterized by (1) having at least 6, preferably 10, more preferably 12, still more preferably 15 or 20, and most preferably at least 30, still more preferably 40, still more preferred 45 consecutive amino acids of the amino acid sequence of TIRC7, and (2) being capable of inhibiting proliferation of mitogen-stimulated PBMCs in an assay as described in Example 1.

Figure 1:
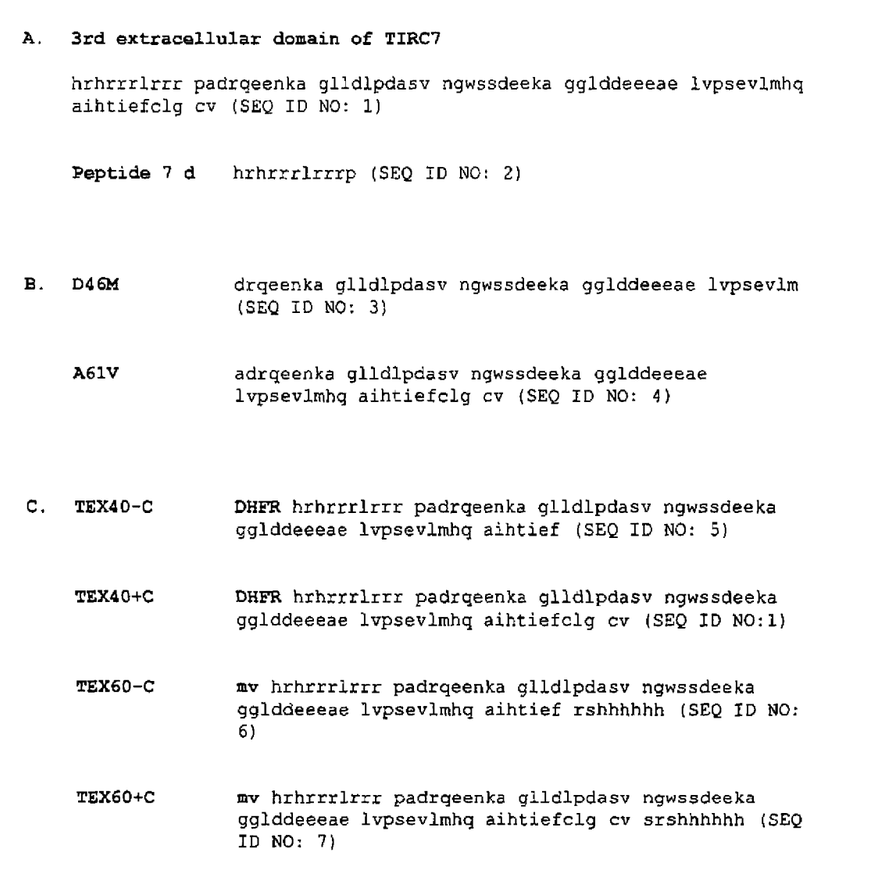
FIG. 1: A. TIRC7 third extracellular domain. B. Synthetic short peptides. C. TIRC7 extracellular domain expressed in E. coli. +C and −C in part C of the Figure denotes the presence or absence of the C-terminus of TIRC7. The third extracellular domain (nucleotide position 1857 to 2057 with respect to the TIRC7 cDNA sequence disclosed in gene bank accession no AF 025374, ATG at nucleotide position 537) was cloned and expressed in E. coli either with or without the C-terminus of TIRC7 (nucleotide position 2058 to 2616, i.e. an additional fragment of 558 bp) including the intervening transmembrane domain. For the cloning and expression in E. coli conventional vectors and plasmids may be used, e.g. PCR-Script, pQE30, pQE60, pQE40 available from commercial suppliers, e.g. Stratagene, Qiagen.

The term "TIRC7" as used in accordance with the present invention, denotes a protein involved in the signal transduction of T-cell activation and/or proliferation and that, preferably in a soluble form is capable of inhibiting or suppressing T-cell proliferation in response to alloactivation in a mixed lymphocyte culture or in response to mitogens when exogeneously added to the culture. In vitro translated TIRC7 protein is able to efficiently suppress in a dose dependent manner the proliferation of T-cells in response to alloactivation in a mixed lymphocyte culture or in response to mitogens. TIRC7 is known to the person skilled in the art and described, inter alia, in WO99/11782 and in Utku et al., Immunity 9 (1998), 509-518. The third extracellular domain of TIRC7 protein can be determined in accordance with the disclosure in FIG. 1B and FIG. 2 of international application WO99/11782.

In one embodiment the peptide of the present invention is derived from a TIRC7 protein which comprises an amino acid sequence as shown in FIG. 1 (SEQ ID NO: 1), or a fragment thereof. Active peptides could be larger or smaller than the ones specifically described here. While the present peptides described are of about 11 to 72 amino acids, peptides containing a relatively large number of amino acid residues, e.g., up to about 50 or 100 amino acid residues or more, that contain the described peptides, portions thereof, or similar peptides may have biological activity as well. Similarly, peptides smaller than those shown in SEQ ID NOs: 1 to 5 may also have similar biological activity. For example, in one embodiment the peptide of the present invention comprises or consists of the amino acid sequence depicted in SEQ ID NO: 1 from amino acid position 1 to 27. Similarly, peptides with amino acid substitutions or other alterations may block the activities of the described peptides or the parent molecules. Cyclic or otherwise modified forms of the peptides would also be expected to have biological activity. Preferably, the peptides of the present invention have at least the first 6, preferably at least the first 10, and most preferred at least the first 11 amino acids of SEQ ID NO: 1.

In addition, the present invention provides isolated peptides that include an amino acid sequence represented by SEQ ID NOs: 1 to 5 or analogs thereof that modulate the function of at least one TIRC7 protein and/or at least one ligand thereof. These amino acid sequences can also form a part of a larger peptide. Additionally, they can be used in various combinations in any one peptide. Preferably, the present invention provides isolated peptides represented by SEQ ID NOs: 1 to 5 or analogs thereof. It is believed that these portions of certain of the peptides described herein contribute significantly to the activity of the peptides.

The present peptides are preferably capable of modulating, preferably inhibiting proliferation of peripheral blood mononuclear cells (PBMCs). Preferably, the peptides of the present invention modulate at least one of the following (which are functions of TIRC7 proteins and/or ligands thereof): activation of neutrophils; activation or inhibition of T-cells, B-cells, NK cells, LAK cells, dendritic cells, or other immune system cells; proliferation and/or differentiation of T-cells, B-cells, NK cells, LAK cells, dendritic cells, or other immune system cells; proliferation and/or differentiation of epithelial cells such as breast or intestinal/colonic epithelium cells or keratinocytes. In addition these peptides are preferably capable of altering homotypic and/or heterotypic adhesion among TIRC7 proteins (i.e., TIRC7 family members) or adhesion of TIRC7 proteins to other TIRC7 ligands.

The present invention also provides peptide conjugates. The ability of peptides complexed with carrier molecules or structures, such as microbeads, liposomes, biological carrier molecules, synthetic polymers, biomaterials, and cells, thereby forming peptide conjugates is shown to impart the larger structure with the ability to bind to cells expressing TIRC7 or its ligand. Such peptide conjugates bind to cells expressing a TIRC7 protein or a TIRC7 ligand.

The peptides or peptide conjugates of the present invention can also include molecules for labeling (i.e., labels such as fluorescence tags, magnetic resonance tags, radioactive tags, enzymatic tags). In this way, these can be used in diagnostic methods to detect specific targets in vivo or in vitro.

The present invention also provides a method of modulating (e.g., activating or inhibiting) immune cell (e.g., T-cells, B-cells, NK cells, LAK cells, or dendritic cells) activation, proliferation, and/or differentiation that includes contacting an immune cell with a peptide or peptide conjugate described above. Preferably, the peptide is one of those indicated as represented by SEQ ID NOs: 1, 2, 3, 4, 5, 6 or 7.

In addition, some peptides differ from these peptides by one or several amino acids and could compete with these active peptides or the natural TIRC7 protein or ligand thereof for certain biological activities.

Another method involves delivering a therapeutically active agent to a patient. The method includes administering at least one peptide or peptide conjugate comprising a peptide and the therapeutically active agent to a patient, wherein the peptide preferably includes an amino acid sequence represented by SEQ ID NOs: 1 to 5 or analogs thereof. Preferably, the therapeutically active agent is selected from drugs, DNA sequences, RNA sequences, proteins, lipids, and combinations thereof. More preferably, the therapeutically active agent is an antibacterial agent, antiinflammatory agent, or antineoplastic agent.

Yet another method of the present invention involves altering an immune response. The method includes contacting immune system cells with at least one peptide or peptide conjugate of the present invention described above.

The methods described herein can be carried out in vitro or in vivo. The peptides can be used alone or in various combinations as well as in peptide conjugates. They are used in amounts that provide the desired effect. These amounts can be readily determined by one of skill in the art. Preferably, for each of the methods of the present invention, useful peptides are represented by SEQ ID NOs: 1, 2, 3, 4, 5, 6 or 7.

As used herein, "a" or "an" refers to one or more of the term modified. Thus, the compositions and methods of the present invention include one or more peptides. Also, herein when a peptide is said to include an amino acid sequence the polypeptide preferably includes an amino acid sequence as represented by SEQ ID NOs: 1 to 5 or analogs thereof, the peptide can include one or more of the sequences specified.

"Amino acid" is used herein to refer to a chemical compound with the general formula: $NH_2$—CRH—COOH, where R, the side chain, is H or an organic group. Where R is an organic group, R can vary and is either polar or nonpolar (i.e., hydrophobic). The amino acids of this invention can be naturally occurring or synthetic (often referred to as nonproteinogenic).

As used herein, an organic group is a hydrocarbon group that is classified as an aliphatic group, a cyclic group or combination of aliphatic and cyclic groups.

The term "aliphatic group" means a saturated or unsaturated linear or branched hydrocarbon group. This term is used to encompass alkyl, alkenyl, and alkynyl groups, for example.

The term "cyclic group" means a closed ring hydrocarbon group that is classified as an alicyclic group, aromatic group, or heterocyclic group.

The term "alicyclic group" means a cyclic hydrocarbon group having properties resembling those of aliphatic groups.

The term "aromatic group" refers to mono- or polycyclic aromatic hydrocarbon groups. As used herein, an organic group can be substituted or unsubstituted.

The terms "polypeptide" and "peptide" as used herein, are used interchangeably and refer to a polymer of amino acids. These terms do not connote a specific length of a polymer of amino acids. Thus, for example, the terms oligopeptide, protein, and enzyme are included within the definition of polypeptide or peptide, whether produced using recombinant techniques, or chemical or enzymatic synthesis, or naturally occurring. This term also includes polypeptides that have been modified or derivatized, such as by glycosylation, acetylation, phosphorylation, and the like.

Herein, "isolated" as it refers to peptides (i.e., polypeptides) means that the peptides are derived from naturally occurring proteins or other polypeptides and free from other biological material or they are synthesized, either recombinantly or chemically.

The following abbreviations are used throughout the application:
A=Ala=Alanine T=Thr Threonine
V=Val=Valine C=Cys=Cysteine
L=Leu=Leucine Y=Tyr=Tyrosine
I=IIe=Isoleucine N=Asn=Asparagine
P=Pro=Proline Q=Gln=Glutamine
F=Phe=Phenylalanine D=Asp=Aspartic Acid
W=Trp=TryptophanE=Glu=Glutamic Acid
M=Met=Methionine K=Lys=Lysine
G=Gly=Glycine=Arg=Arginine
S=Ser=Serine H=His=Histidine As mentioned before, the present invention provides TIRC7 peptides capable of modulating the immune response. As it was shown by Utku et al (Immunity, 1998) in v/tro-translated protein TIRC7 significantly suppressed the proliferation of activated T-cells in MLR in a dose dependent manner. In order to investigate the effect of TIRC7-peptides on proliferation of stimulated PBMC similar assays were performed using TIRC7-peptides derived from the third extracellular domain of TIRC7 protein.

Thus, the present invention provides isolated peptides derived from TIRC7 that include an amino acid sequence represented by (at least one of) SEQ ID NOs: 1 to 5 or analogs thereof that modulate the function of TIRC7 protein and/or at least one ligand thereof.

As described in Example 1 herein, peptides were tested for their ability to inhibit proliferation of mitomycin-stimulated PBMCs. Therefore, the TIRC7 derived peptides of the present invention were tested in lymphocyte proliferation assays as described in international applications WO99/11782 and WO03/025000, see also supra, and it could surprisingly be shown that synthetic peptides derived from the third extracellular domain of TIRC7 protein are functional in low concentrations and therefore are most suitable for therapeutic applications. Particular advantageous examples are peptides D46M (SEQ ID NO: 3) and A61V (SEQ ID NO: 4), see also FIG. 1. Furthermore, recombinantly produced TIRC7 peptides corresponding to most if not all of the entire third extracellular domain of TIRC7, and optionally further comprising the C-terminal domain of TIRC7 also showed inhibition of proliferation of mitomycin-stimulated PBMCs.

Accordingly, the peptides of the present invention are expected to be useful in the modulation of immune responses. Modulating the immune response, as for example by activating or inhibiting the proliferation and/or differentiation of T-cells, B-cells, NK cells, LAK cells, dendritic cells, monocytes, macrophages or other immune system cells, may be useful in treating autoimmune diseases, allergic diseases, and in transplantation therapies where graft vs. host or host vs. graft effects may be undesirable. The peptides could also be immune stimulants in settings such as cancer, infectious disease, sepsis, wound healing, or immunization. Alternatively, they could be immune suppressants. They could also be used to detect inflammation, and preferably modulate inflammation by activating or inhibiting activation of immune or inflammatory cells. A preferred method involves detecting (and preferably modulating) inflammation in tissues such as inflamed vasculature or leukocytes. In one preferred embodiment the peptide and peptide conjugates are used for inducing or maintaining immune unresponsiveness in a subject. The term "immune unresponsiveness" comprises non-unresponsiveness of immune cell subsets like T-cell or B-cells, NK-cells, monocytes and/or macrophages.

The terms "treatment", "treating" and the like are used herein to generally mean obtaining a desired pharmacological and/or physiological effect. The effect may be prophylactic in terms of completely or partially preventing a disease or symptom thereof and/or may be therapeutic in terms of partially or completely curing a disease and/or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e. arresting its development; or (c) relieving the disease, i.e. causing regression of the disease.

Furthermore, the term "subject" as employed herein relates to animals in need of amelioration, treatment and/or prevention of immunological diseases as disclosed herein. Most preferably said subject is a human.

Thus, the present invention provides peptides derived from the third extracellular domain of TIRC7 peptides that are capable of modulating (i.e., altering by increasing, decreasing, etc.), for example, immune cell activation, cell proliferation, cell differentiation, or binding of TIRC7 to its ligands. Preferably, the present invention provides isolated peptides comprising or consisting of an amino acid sequence indicated SEQ ID NO: 1 (see FIG. 1), or a fragment thereof, for example in one embodiment the peptide of the present invention comprises or consists of the amino acid sequence depicted in SEQ ID NO: 1 from amino acid position 1 to 27. In addition, the present invention provides isolated peptides represented by SEQ ID NOs: 1 to 5.

Furthermore, the peptides of the invention are preferably used for specific inhibition or modulation of IFN-γ dependent immune reactions which refers to ThI type of immune responses associated with transplant rejection, multiple sclerosis, Type I diabetes mellitus or rheumatoid arthritis without a modulatory effect on Th2 immune reactions. Others are believed to possess a least one activity as described herein.

Compositions comprising the polypeptides of this invention can be added to cells in culture (in vitro) or used to treat patients, such as mammals (in vivo). Where the polypeptides are used to treat a patient, the polypeptide is preferably combined in a pharmaceutical composition with a pharmaceutically acceptable carrier such as a larger molecule to promote polypeptide stability or a pharmaceutically acceptable buffer that serves as a carrier for the polypeptide or incorporated in a peptide conjugate that has more than one peptide coupled to a single entity.

The biological activity of the peptides identified here suggests that they have sufficient affinity to make them potential candidates for drug localization to cells expressing the appropriate surface structures. This targeting and binding to cells could be useful for the delivery of therapeutically active agents (including targeting drugs, DNA sequences, RNA sequences, lipids, proteins (e.g., human growth factors)) and gene therapy/gene delivery. More preferably, the therapeutically active agent is an antiinflammatory agent.

Molecules/particles with a specific number of TIRC7 peptides would bind specifically to cells/tissues expressing specific ligand combinations, and therefore could have diagnostic and therapeutic use. Thus, the peptides of the present invention can be labeled (e.g., fluorescent, radioactive, enzyme, nuclear magnetic) and used to detect specific targets in vivo or in vitro including "immunochemistry" like assays in vitro. In vivo they could be used in a manner similar to nuclear medicine imaging techniques to detect tissues, cells, or other material expressing TIRC7 or its ligand.

The peptides of the present invention can be in their free acid form or they can be amidated at the C-terminal carboxylate group. The present invention also includes analogs of TIRC7 peptides of, for example, SEQ ID NOs: 1 to 5, which typically have structural similarity with any one of SEQ ID NOs: 1 to 5. An "analog" of a polypeptide includes at least a portion of the polypeptide, wherein the portion contains deletions or additions of one or more contiguous or noncontiguous amino acids, or containing one or more amino acid substitutions. Substitutes for an amino acid in the polypeptides of the invention are preferably conservative substitutions, which are selected from other members of the class to which the amino acid belongs. An analog can also be a larger peptide that incorporates the peptides described herein. For example, it is well-known in the art of protein biochemistry that an amino acid belonging to a grouping of amino acids having a particular size or characteristic (such as charge, hydrophobicity and hydrophilicity) can generally be substituted for another amino acid without substantially altering the structure of a polypeptide. For the purposes of this invention, conservative amino acid substitutions are defined to result from exchange of amino acids residues from within one of the following classes of residues: Class 1: Ala, Gly, Ser, Thr, and Pro; Class II: Cys, Ser, Thr, and Tyr; Class III: Glu, Asp, Asn, and Gln (carboxyl group containing side chains): Class IV: His, Arg, and Lys (representing basic side chains); Class V: He, Val, Leu, Phe, and Met (representing hydrophobic side chains); and Class VI: Phe, Trp, Tyr, and His (representing aromatic side chains). The classes also include other related amino acids such as halogenated tyrosines in Class VI.

Polypeptide analogs, as that term is used herein, also include modified polypeptides. Modifications of polypeptides of the invention include chemical and/or enzymatic derivatizations at one or more constituent amino acid, including side chain modifications, backbone modifications, and N- and C-terminal modifications including acetylation, hydroxylation, methylation, amidation, and the attachment of carbohydrate or lipid moieties, cofactors, and the like.

In a preferred embodiment the peptide of the present invention comprises one of the group of D-isomer amino acids, L-isomer amino acids, or a combination thereof. The preparation of peptides comprising D-isomer amino acids is described for example in Schumacher, Science 271 (1996), 1854-1857.

A preferred peptide analog is characterized by having at least one of the biological activities described herein. Such an analog is referred to herein as a "biologically active analog" or simply "active analog". The biological activity of a peptide can be determined, for example, as described in Example 1.

The peptides of the invention may be synthesized by the solid phase method using standard methods based on either t-butyloxycarbonyl (BOC) or 9 fluorenylmethoxy-carbonyl (FMOC) protecting groups. This methodology is described by G. B. Fields et al. in Synthetic Peptides: A User's Guide, W. M. Freeman & Company, New York, N.Y., pp. 77-183 (1992). The present peptides may also be synthesized via recombinant techniques well known to those skilled in the art. For example, U.S. Pat. No. 5,595,887 describes methods of forming a variety of relatively small peptides through expression of a recombinant gene construct coding for a fusion protein which includes a binding protein and one or more copies of the desired target peptide. After expression, the fusion protein is isolated and cleaved using chemical and/or enzymatic methods to produce the desired target peptide.

Accordingly, in one preferred embodiment the peptide of the present invention comprises a heterologous amino acid or amino acid sequence, e.g. a tag, at its N- and/or C-terminus, e.g. to facilitate purification of the peptide of the invention, said heterologous amino acid sequence may include, but is not limited to Arg-tag, B-tag (VP7 protein region of bluetongue virus), calmodulin-binding peptide, CAT (Chloramphenicol acetyltransferase), CBP (Cellulose-binding domains), Chitin-binding domain, c-myc-tag, DHFR (Dihydrofolate reductase), DsbA, FLAG-tag, Galactose-binding protein, GST (glutathione S-transferase), HAT-tag, His-tag, HSV-tag, KSI, lacL (β-galactosidase), lac repressor, maltose-binding protein, MBP (Maltose-binding protein), my, NusA, Polyaspartic acid, Polyphenylalanine, S-tag, SBP-tag, Staphylococcal protein A, Streptococcal protein G, Strep-tag, Ubiquitin, T7-tag, T7geneIO, thioredoxin, His-patch thioredoxin or trpE.

In a preferred embodiment the peptide of the present invention comprises the amino acid sequence represented in SEQ ID NO: 6 or 7 (see FIG. 1).

The peptides of the present invention may be employed in a monovalent state (e.g., free peptide or peptide coupled to a carrier molecule or structure). The peptides may also be employed as conjugates having more than one (same or different) peptide bound to a single carrier molecule. The carrier molecule or structure may be microbeads, liposomes, biological carrier molecule (e.g., a glycosaminoglycan, a proteoglycan, albumin, or the like), a synthetic polymer (e.g., a polyalkyleneglycol or a synthetic chromatography support), biomaterial (e.g., a material suitable for implantation into a mammal or for contact with biological fluids as in an extracorporeal device), or other cell. Typically, ovalbumin, human serum albumin, other proteins, polyethylene glycol, or the like are employed as the carrier. Such modifications may increase the apparent affinity and/or change the stability of a peptide. The number of peptide fragments associated with or bound to each carrier can vary. In addition, as mentioned above, the use of various mixtures and densities of the peptides described herein may allow the production of complexes that have specific binding patterns in terms of preferred ligands. The peptides can be conjugated to other polypeptides using standard methods known to one of skill in the art. Conjugates can be separated from free peptide through the use of gel filtration column chromatography or other methods known in the art.

For instance, peptide conjugates may be prepared by treating a mixture of peptides and carrier molecules (or structures) with a coupling agent, such as a carbodiimide. The coupling agent may activate a carboxyl group on either the peptide or the carrier molecule (or structure) so that the carboxyl group can react with a nucleophile (e.g. an amino or hydroxyl group) on the other member of the peptide conjugate, resulting in the covalent linkage of the peptide and the carrier molecule (or structure).

As another example, peptides may be coupled to biotin-labeled polyethylene glycol and then coupled to avidin containing compounds. In the case of peptides coupled to other entities, it should be understood that the designed activity may depend on which end of the peptide is coupled to the entity.

The present invention also provides a composition that includes one or more active agents (i.e., peptides) of the invention and one or more pharmaceutically acceptable carriers. One or more polypeptides with demonstrated biological activity can be administered to a patient in an amount alone or together with other active agents and with a pharmaceutically acceptable buffer. The polypeptides can be combined with a variety of physiologically acceptable carriers for delivery to a patient including a variety of diluents or excipients known to those of ordinary skill in the art. For example, for parenteral administration, isotonic saline is preferred. For topical administration, a cream, including a carrier such as dimethylsulfoxide (DMSO), or other agents typically found in topical creams that do not block or inhibit activity of the peptide, can be used. Other suitable carriers include, but are not limited to alcohol, phosphate buffered saline, and other balanced salt solutions.

The formulations may be conveniently presented in unit dosage form and may be prepared by any of the methods well known in the art of pharmacy. Preferably, such methods include the step of bringing the active agent into association with a carrier that constitutes one or more accessory ingredients.

The methods of the invention include administering to a patient, preferably a mammal, and more preferably a human, the composition of the invention in an amount effective to produce the desired effect. The peptides can be administered as a single dose or in multiple doses. Useful dosages of the active agents can be determined by comparing their in vitro activity and the in vivo activity in animal models. Methods for extrapolation of effective dosages in mice, and other animals, to humans are known in the art.

In a preferred embodiment, the pharmaceutical composition of the present invention comprises at least one second agent, preferably an agent which inhibits T-cell stimulation depending on the intended use. Such agents include, for example, molecules that are capable of blocking or mimicking receptor/ligand interaction or the like which leads to T-cell suppression.

Such agents comprise those blocking the activity of, e.g., costimulatory molecules, such as anti TIRC7 antibodies, and TNF-α blocking agents, e.g. antibodies, integrins, Ig-superfamily molecules, selectins as well as drugs blocking chemokines and their respective receptor interactions, drugs blocking IL2/IL2-receptor interaction and other conventional immunosuppressive drugs such as IL-2R mAbs, IL-Toxins and IL-Muteins. Examples for costimulatory molecules and their ligands are described in the prior art, e.g., in Schwartz, Cell 71 (1992), 1065-1068. The interruption of the receptor/ligand interactions by using mAbs or soluble CTLA41g for the interaction between CD28 to the B7-2 and CTLA4 to B7-1 and B7-2 are described in Blazar, J. Immunol. 157 (1996), 3250-3259; Bluestone, Immunity 2 (1995), 555-559; Linsley, Science 257 (1992), 792-95. Examples for blocking the receptor/ligand interaction by using mAbs to CD40 or CD40L are reported by Burden, Nature 381 (1996), 434-435; Kirk, Proc. Natl. Acad. Sci. USA 94 (1997), 8789-8794. CD2 antigen and its ligand LFA-3 are described in Bagogui Li et al., review in Adhesion Molecules, Fusion proteins, Novel Peptides, and Monoclonal Antibodies, Recent Developments in Transplantation Medicine, Vol. II, 1995; Physicians & Scientists Publishing Co., Inc. and blocking of their interaction by using of mAbs (anti-Leu-5b, OKTI I, TI I) is reported in Bromberg, Transplantation 51 (1991) 219-225 or CD2.1gGI fusion protein. The use of monoclonal Abs agains CD4 molecule is described in Cosimi, Surgery 108 (1990), 406-414. CD47 blockade by mAbs is described by Rheinhold, J. Exp. Med. 185 (1997), 1-11. Integrins and Ig-superfamily molecules include LFA-I with its ligand ICAM-I, -2, -3, Mac-1 with ist ligand 1 CAM-I, -3; ICAM-I with its ligand LFA-I, Mac-1, CD43; ICAM-2 with ist ligand LFA-I; ICAM-3 with its ligand LEA-I, Mac-1; VLA4 and VCAM-1 see, e.g., David, Adams, review in Adhesion Molecules, Fusion proteins, Novel Peptides, and Monoclonal Antibodies, Recent Developments in Transplantation Medicine, Vol. II, 1995, Physicians&Scientists Publishing Co., Inc.; Isobe, Science, 255 (1992), 1 125-1127; Cosimi, J. Immunology 144 (1990), 4604-4612; Hynes, Cell 69 (1992), 11-25.

Furthermore selectively interfering agents with VLA-4 mAbs to the alpha4 integrin chain (CD49d) can be used, beta1 integrin chain (CD29), or an activation-induced neo-epitope of VLA-4 as well as soluble VLA-4 ligands such as soluble fibronectin or its relevant peptide (GPEILDVPST (SEQ ID NO:8)), or soluble VCAM-1 or its relevant peptide. More selectively blocking agents are antisense oligonucleotides, designed to selectively hybridize with cytoplasmic alpha4, beta1, or VCAM-I mRNA; Fedoseyeva, J. Immunol. 57 (1994), 606-612.

Another example is the drug pentoxifylline (PTX) that is able to block expression of VCAM-I; Besler, J. Leukoc. Biol. 40 (1986), 747-754. Furthermore, VCAM-I mAb, M/K-2, anti-murine, for example could prolong allograft survival, Orosz, Transplantation, 56 (1993), 453-460.

Blocking of members of the integrin family and their ligands by using mAbs is described in Kupiec-Weglinski, review in Adhesion Molecules, Fusion proteins, Novel Peptides, and Monoclonal Antibodies, Recent Developments in Transplantation Medicine, Vol. II, 1995, Physicians&Scientists Publishing Co., Inc.

Selectins, e.g., L-selectin (CD62L), E-selectin (CD62E), P-selectin (CD62P) have been described in Forrest and Paulson, Selectin family of adhesion molecules. In: Granger and Schmid-Schonbein, eds. Physiology and Pathophysiology of Leukocyte Adhesion. New York, Oxford Press, 1995, pp 68-146.

The combination of conventional immunosuppressive drugs, e.g., ATG, ALG, OKT3, Azathioprine, Mycophenylate, Mofetyl, Cyclosporin A, FK.506, Sirolimus (Rapamune), Corticosteroids may be used as described in Cosimi, Transplantation 32 (1981), 535-539; Shield, Transplantation 38 (1984), 695-701, and Graft, June 2001, Vol 4 (4).

The interruption of chemokines and interactions with their respective receptor by using mAbs is reviewed in Luster, Chemokines-chemotactic cytokines that mediate inflammation, New Engl. J. Med. February (1998), 436-445.

Thus, any agent as defined above and referenced by way of example can be used in accordance with the pharmaceutical composition of the invention or the methods and uses described herein.

The agents of the present invention are preferably formulated in pharmaceutical compositions and then, in accordance with the methods of the invention, administered to a patient, such as a human patient, in a variety of forms adapted to the chosen route of administration. The formulations include, but are not limited to, those suitable for oral, rectal, vaginal, topical, nasal, ophthalmic, or parental (including subcutaneous, intramuscular, intraperitoneal, intratumoral, intraorgan, intraarterial and intravenous) administration. Formulations suitable for parenteral administration conveniently include a sterile aqueous preparation of the active agent, or dispersions of sterile powders of the active agent, which are preferably isotonic with the blood of the recipient. Absorption of the active agents over a prolonged period can be achieved by including agents for delaying, for example, aluminum monostearate and gelatin.

Formulations of the present invention suitable for oral administration may be presented as discrete units such as tablets, troches, capsules, lozenges, wafers, or cachets, each containing a predetermined amount of the active agent as a powder or granules, as liposomes containing the active agent, or as a solution or suspension in an aqueous liquor or non-aqueous liquid such as a syrup, an elixir, an emulsion, or a draught. Such compositions and preparations typically contain at least about 0.1 wt-% of the active agent. The amount of polypeptide (i.e., active agent) is such that the dosage level will be effective to produce the desired result in the patient.

Aerosol formulations such as nasal spray formulations include purified aqueous or other solutions of the active agent with preservative agents and isotonic agents. Such formulations are preferably adjusted to a pH and isotonic state compatible with the nasal mucous membranes. Formulations for rectal or vaginal administration may be presented as a suppository with a suitable carrier.

Furthermore, the present invention relates to the use of a peptide comprising an amino acid sequence derived from the third extracellular domain of TIRC7 protein for the preparation of a pharmaceutical composition for inhibition of an immune response, preferably for the treatment of graft versus host disease, autoimmune diseases, allergic diseases, infectious diseases, sepsis, for the treatment of tumors, for the improvement of wound healing or for inducing or maintaining immune unresponsiveness in a subject.

Further examples of disorders to be treated in accordance with the method of the present invention include, but are not limited to, an immune system disorder such as inflammation, actinic keratosis, acquired immunodeficiency syndrome (AIDS), Addison's disease, adult respiratory distress syndrome, allergies, ankylosing spondylitis, amyloidosis, anemia, arteriosclerosis, asthma, atherosclerosis, autoimmune hemolytic anemia, autoimmune thyroiditis, bronchitis, bursitis, cholecystitis, cirrhosis, contact dermatitis, Crohn's disease, atopic dermatitis, dermatomyositis, diabetes mellitus, emphysema, erythroblastosis fetalis, erythema nodosum, atrophic gastritis, glomerulonephritis, Goodpasture's syndrome, gout, Graves' disease, Hashimoto's thyroiditis, paroxysmal nocturnal hemoglobinuria, hepatitis, hypereosinophilia, irritable bowel syndrome, episodic lymphopenia with lymphocytotoxins, mixed connective tissue disease (MCTD), multiple sclerosis, myasthenia gravis, myocardial or pericardial inflammation, myelofibrosis, osteoarthritis, osteoporosis, pancreatitis, polycythemia vera, polymyositis, psoriasis, Reiter's syndrome, rheumatoid arthritis, scleroderma, Sjgren's syndrome, systemic anaphylaxis, systemic lupus erythematosus, systemic sclerosis, primary thrombocythemia, thrombocytopenic purpura, ulcerative colitis, uveitis, Werner syndrome, complications of cancer, hemodialysis, and extracorporeal circulation, trauma, and hematopoietic cancer including lymphoma, leukemia, and myeloma; a reproductive disorder such as a disorder of prolactin production, infertility, including tubal disease, ovulatory defects, and endometriosis, a disruption of the estrous cycle, a disruption of the menstrual cycle, polycystic ovary syndrome, ovarian hyperstimulation syndrome, an endometrial or ovarian tumor, a uterine fibroid, autoimmune disorders, an ectopic pregnancy, and teratogenesis, cancer of the breast, fibrocystic breast disease, and galactorrhea, a disruption of spermatogenesis, abnormal sperm physiology, cancer of the testis, cancer of the prostate, benign prostatic hyperplasia, prostatitis, Peyronie's disease, impotence, carcinoma of the male breast, and gynecomastia; a nervous system disorder such as epilepsy, ischemic cerebrovascular disease, stroke, cerebral neoplasms, Alzheimer's disease, Pick's disease, Huntington's disease, dementia, Parkinson's disease and other extrapyramidal disorders, amyotrophic lateral sclerosis and other motor neuron disorders, progressive neural muscular atrophy, retinitis pigmentosa, hereditary ataxias, multiple sclerosis and other demyelinating diseases, bacterial and viral meningitis, brain abscess, subdural empyema, epidural abscess, suppurative intracranial thrombophlebitis, myelitis and radiculitis, viral central nervous system disease, prion diseases including kuru, Creutzfeldt-Jakob disease, and Gerstmann-Straussler-Scheinker syndrome, fatal familial insomnia, nutritional and metabolic diseases of the nervous system, neurofibromatosis, tuberous sclerosis, cerebelloretinal hemangioblastomatosis, encephalotrigeminal syndrome, mental retardation and other developmental disorders of the central nervous system, cerebral palsy, neuroskeletal disorders, autonomic nervous system disorders, cranial nerve disorders, spinal cord diseases, muscular dystrophy and other neuromuscular disorders, peripheral nervous system disorders, dermatomyositis and polymyositis, inherited, metabolic, endocrine, and toxic myopathies, myasthenia gravis, periodic paralysis, mental disorders including mood, anxiety, and schizophrenic disorders, akathesia, amnesia, catatonia, diabetic neuropathy, tardive dyskinesia, dystonias, paranoid psychoses, postherpetic neuralgia, and Tourette's disorder; a cell signaling disorder including endocrine disorders such as disorders of the hypothalamus and pituitary resulting from lesions such as primary brain tumors, adenomas, infarction associated with pregnancy, hypophysectomy, aneurysms, vascular malformations, thrombosis, infections, immunological disorders, and complications due to head trauma; disorders associated with hyperpituitarism including acromegaly, giantism, and syndrome of inappropriate antidiuretic hormone (ADH) secretion (SIADH) often caused by benign adenoma; disorders associated with hypothyroidism including goiter, myxedema, acute thyroiditis associated with bacterial infection; disorders associated with hyperparathyroidism including Conn disease (chronic hypercalcemia); pancreatic disorders such as Type I or Type II diabetes mellitus and associated complications; disorders associated with the adrenals such as hyperplasia, carcinoma, or adenoma of the adrenal cortex, hypertension associated with alkalosis; disorders associated with gonadal steroid hormones such as: in women, abnormal prolactin production, infertility, endometriosis, perturbations of the menstrual cycle, polycystic ovarian disease, hyperprolactinemia, isolated gonadotropin deficiency, amenorrhea, galactorrhea, hermaphroditism, hirsutism and virilization, breast cancer, and, in postmenopausal women, osteoporosis; and, in men, Leydig cell deficiency, male climacteric phase, and germinal cell aplasia, hypergonadal disorders associated with Leydig cell tumors, androgen resistance associated with absence of androgen receptors, syndrome of 5 a-reductase, and gynecomastia; and a cell proliferative disorder such as actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus.

In a still further aspect the present invention relates to the use of a therapeutic agent, preferably immunosuppressive agent for the prevention or treatment of any one of the above-mentioned diseases of a subject, wherein said subject has been positively tested.

These and other embodiments are disclosed and encompassed by the description and examples of the present invention. Further literature concerning any one of the materials, methods, uses and compounds to be employed in accordance with the present invention may be retrieved from public libraries and databases, using for example electronic devices. For example the public database "Medline" may be utilized, which is hosted by the National Center for Biotechnology Information and/or the National Library of Medicine at the National Institutes of Health. Further databases and web addresses, such as those of the European Bioinformatics Institute (EBI), which is part of the European Molecular Biology Laboratory (EMBL) are known to the person skilled in the art and can also be obtained using internet search engines. An overview of patent information in biotechnology and a survey of relevant sources of patent information useful for retrospective searching and for current awareness is given in Berks, TIBTECH 12 (1994), 352-364.

Several documents are cited throughout the text of this specification. The contents of all cited references (including literature references, issued patents, published patent applications as cited throughout this application and manufacturer's specifications, instructions, etc) are hereby expressly incorporated by reference; however, there is no admission that any document cited is indeed prior art as to the present invention.

The above disclosure generally describes the present invention. A more complete understanding can be obtained by reference to the following specific examples which are provided herein for purposes of illustration only and are not intended to limit the scope of the invention.

EXAMPLES

Detailed descriptions of conventional methods, such as those employed herein can be found in the cited literature; see also "The Merck Manual of Diagnosis and Therapy" Seventeenth Ed. ed by Beers and Berkow (Merck & Co., Inc. 2003).

The practice of the present invention will employ, unless otherwise indicated, conventional techniques of cell biology, cell culture, molecular biology, transgenic biology, microbiology, recombinant DNA, and immunology, which are within the skill of the art.

Methods in molecular genetics and genetic engineering are described generally in the current editions of Molecular Cloning: A Laboratory Manual, (Sambrook et al., (1989) Molecular Cloning: A Laboratory Manual, 2nd ed., Cold Spring Harbor Laboratory Press); DNA Cloning, Volumes I and II (Glover ed., 1985); Oligonucleotide Synthesis (Gait ed., 1984); Nucleic Acid Hybridization (Hames and Higgins eds. 1984); Transcription And Translation (Hames and Higgins eds. 1984); Culture Of Animal Cells (Freshney and Alan, Liss, Inc., 1987); Gene Transfer Vectors for Mammalian Cells (Miller and Calos, eds.); Current Protocols in Molecular Biology and Short Protocols in Molecular Biology, 3rd Edition (Ausubel et al., eds.); and Recombinant DNA Methodology (Wu, ed., Academic Press). Gene Transfer Vectors For Mammalian Cells (Miller and Calos, eds., 1987, Cold Spring Harbor Laboratory); Methods In Enzymology, Vols. 154 and 155 (Wu et al., eds.); Immobilized Cells And Enzymes (IRL Press, 1986); Perbal, A Practical Guide To Molecular Cloning (1984); the treatise, Methods In Enzymology (Academic Press, Inc., N.Y.); Immunochemical Methods In Cell And Molecular Biology (Mayer and Walker, eds., Academic Press, London, 1987); Handbook Of Experimental Immunology, Volumes I-IV (Weir and Blackwell, eds., 1986). Reagents, cloning vectors, and kits for genetic manipulation referred to in this disclosure are available from commercial vendors such as BioRad, Stratagene, Invitrogen, and Clontech. General techniques in cell culture and media collection are outlined in Large Scale Mammalian Cell Culture (Hu et al., Curr. Opin. Biotechnol. 8 (1997), 148); Serum-free Media (Kitano, Biotechnology 17 (1991), 73); Large Scale Mammalian Cell Culture (Curr. Opin. Biotechnol. 2 (1991), 375); and Suspension Culture of Mammalian Cells (Birch et al, Bioprocess Technol. 19 (1990), 251); Extracting information from cDNA arrays, Herzel et al., CHAOS 11, (2001), 98-107.

The example illustrates the invention.

Example 1

Assessment of Potency of TIRC7 Derived Peptides to Inhibit Cell Proliferation

Freshly isolated PBMC were inactivated with mitomycin (stimulator), or stained with CFSE (responder). Cells were incubated for 6 days with the peptides as described in FIG. 1, dissolved in PBS and titrated to pH 7.3. Subsequently, an in vitro assay, mixed lymphocyte reaction (MLR), was performed essentially as described in international applications WO99/11782 and WO03/025000 to analyze the potency of the tested TIRC7 derived peptides to inhibit the immune response. For all peptides shown in FIG. 1 substantial inhibition of proliferation could be observed. This demonstrates that synthetic peptides as well as recombinantly produced peptides which comprise an amino acid sequence of the third extracellular domain of TIRC7 protein are biologically active in suppressing the activity of immune cells and thus have therapeutic utility.

The invention claimed is:

1. A peptide consisting of up to 100 amino acid residues, wherein said peptide is capable of inhibiting proliferation of peripheral blood mononuclear cells, wherein said peptide comprises a fragment of the amino acid sequence from the third extracellular domain of T cell immune response cDNA 7 protein, and wherein said peptide comprises at least the first 10 amino acids of SEQ ID NO: 1, and wherein said peptide is conjugated to a carrier molecule or structure, or to a label.

2. The peptide of claim 1, wherein said peptide comprises at least one amino acid selected from the group consisting of D-isomer amino acids and L-isomer amino acids.

3. The peptide of claim 1, further comprising a heterologous amino acid or amino acid sequence of at least one of its N- and C-terminus.

4. The peptide of claim 1, wherein said heterologous amino acid sequence comprising a His-tag or DHFR.

5. The peptide of claim 1, wherein said peptide comprises the amino acid sequence of SEQ ID NO:6 or 7.

6. A composition comprising at least one peptide of claim 1.

7. The composition of claim 6 which is a pharmaceutical composition and further comprises a pharmaceutically acceptable carrier.

8. The pharmaceutical composition of claim 7 further comprising an immunosuppressive.

9. The peptide, according to claim 1, wherein the carrier molecule or structure is selected from the group consisting of microbeads, liposomes, biological carrier molecules, synthetic polymers, biomaterials, and cells.

10. The peptide, according to claim 1, wherein the label is selected from the group consisting of fluorescence tags, magnetic resonance tags, radioactive tags and enzymatic tags.

* * * * *

UNITED STATES PATENT AND TRADEMARK OFFICE
CERTIFICATE OF CORRECTION

PATENT NO.        : 9,096,654 B2                           Page 1 of 1
APPLICATION NO.   : 13/338771
DATED             : August 4, 2015
INVENTOR(S)       : Nalan Utku It is certified that error appears in the above-identified patent and that said Letters Patent is hereby corrected as shown below:

In the Specification

Column 10,
Line 9, "LEA-I" should read --LFA-I--.

Column 10,
Line 9, "VCAM-1" should read --VCAM-I--.

Column 10,
Line 21, "VCAM-1" should read --VCAM-I--.

Signed and Sealed this
Twenty-first Day of June, 2016

Michelle K. Lee
*Director of the United States Patent and Trademark Office*